(12) United States Patent
Esrock

(10) Patent No.: US 6,250,921 B1
(45) Date of Patent: Jun. 26, 2001

(54) FITTING FOR DENTAL SYRINGE

(76) Inventor: Bernard S. Esrock, 460-B Sovereign Ct., Baldwin, MO (US) 63011

(*) Notice: Subject to any disclaimer, the term of this patent is extended or adjusted under 35 U.S.C. 154(b) by 0 days.

(21) Appl. No.: 09/471,456

(22) Filed: Dec. 22, 1999

(51) Int. Cl.$^7$ .................................................. A61C 17/02

(52) U.S. Cl. .............................................. 433/80; 433/88

(58) Field of Search .................................. 433/80, 85, 88, 433/84, 89, 126, 147; 601/162; 285/39

(56) References Cited

U.S. PATENT DOCUMENTS

| 3,698,088 | 10/1972 | Austin, Jr. . |
| 4,026,025 | 5/1977 | Hunt . |
| 4,133,564 | 1/1979 | Sarson et al. ......................... 285/321 |
| 4,149,315 | 4/1979 | Page, Jr. et al. . |
| 4,193,616 | 3/1980 | Sarson et al. ........................... 285/39 |
| 4,248,589 | 2/1981 | Lewis ...................................... 433/80 |
| 4,508,369 | 4/1985 | Mode ...................................... 285/39 |
| 4,621,842 | 11/1986 | Kowal et al. ........................ 285/322 |
| 4,712,813 | 12/1987 | Passerell et al. ..................... 285/250 |
| 4,807,911 | 2/1989 | Short .................................... 285/323 |

(List continued on next page.)

OTHER PUBLICATIONS

Norgren publication entitled, "Norgren Series 12 Inch Push–In Tube Fittings" published 05/96.

Alkon publication entitled, "Alkon Series AQ Push–In Tube Fittings," publication prior to 09/99.

Parker Hannifan publication entitled, "Parker Prestolok/Prestolok II Fitings," published prior to 09/99.

Pisco Pneumatic Equipment publication entitled, "Pisco Pnuematic Equipment" published prior to 09/99.

Nycoil publication entitled, "Push–In Tube Fittings" published prior to 09/99.

SMC publication entitled, "SMC Inch–size One–Touch Fittings Series KQ" published prior to 09/99.

Imperial Eastman publication entitled, "Omega Flo" published prior to 9/99.

Camozzi Pneumatics publication entilted, "Pro Fit Super–Rapid Pro fit Fittings for Plastic Tube" published prior to 09/99.

Dana publication entitled, "Push Connect" published prior to 09/99.

Legris publication entitled, "Advantages LF3000 Push–to–Connect Fittings" published prior to 09/99.

Primary Examiner—Gene Mancene
Assistant Examiner—Melba Bumgarner
(74) Attorney, Agent, or Firm—Senniger, Powers, Leavitt & Roedel

(57) ABSTRACT

In combination, a syringe tip and a fitting for releasably connecting the tip to a hand piece for delivering a fluid forward to a mouth of a patient. The hand piece has a passageway for delivering the fluid to a discharge end of the hand piece. The syringe tip includes an elongate tube having an exterior surface and an interior passage extending through the tube for transporting the fluid to the patient, the exterior surface of the tip including a portion having a generally constant size and uniform shape. The fitting includes a body adapted to attach to the hand piece adjacent the discharge end, the body having a central opening sized and shaped for receiving the portion of the tip. The fitting also includes a gripping mechanism mounted in the opening having a plurality of locking fingers disposed around the opening. Each of the plurality of fingers includes a tooth extending inwardly into the opening and having a rearward facing point adapted to releasably engage the portion of the exterior surface of the tip when the tip is received in the opening and to prevent ejection of the tip from the opening due to forces applied to the tip by the fluid being transported through the tube to the patient, thereby to secure the tip to the hand piece when the teeth engage the portion of the tip.

16 Claims, 4 Drawing Sheets

U.S. PATENT DOCUMENTS

| | | | |
|---|---|---|---|
| 4,900,068 | 2/1990 | Law | 285/161 |
| 4,975,054 | 12/1990 | Esrock | 433/80 |
| 4,984,984 | 1/1991 | Esrock | 433/88 |
| 5,048,872 | 9/1991 | Gehring | 285/92 |
| 5,049,071 | 9/1991 | Davis et al. | 433/80 |
| 5,125,835 | 6/1992 | Young | 433/80 |
| 5,236,356 | 8/1993 | Davis et al. | 433/80 |
| 5,242,300 | 9/1993 | Esrock | 433/80 |
| 5,286,065 | 2/1994 | Austin et al. | 285/23 |
| 5,306,146 | 4/1994 | Davis et al. | 433/80 |
| 5,342,195 | 8/1994 | Davis et al. | 433/80 |
| 5,370,423 | 12/1994 | Guest | 285/39 |
| 5,460,619 | 10/1995 | Esrock | 604/280 |
| 5,468,027 | 11/1995 | Guest | 285/319 |
| 5,489,205 | 2/1996 | Davis et al. | 433/80 |
| 5,507,537 | 4/1996 | Meisinger et al. | 285/312 |
| 5,580,100 * | 12/1996 | Umezawa et al. | 285/39 |
| 5,591,389 | 1/1997 | Esrock | 264/171.12 |
| 5,722,696 * | 3/1998 | Taneya | 285/39 |
| 5,772,433 | 6/1998 | Esrock | 433/80 |
| 5,927,975 | 7/1999 | Esrock | 433/80 |

* cited by examiner

FITTING FOR DENTAL SYRINGE

BACKGROUND OF THE INVENTION

This invention relates generally to dental syringes, and more particularly to a fitting for releasably connecting a syringe tip to a hand piece for delivering a fluid to a mouth of a patient.

Dental syringes are hand-held devices for discharging fluids, such as pressurized air and water, into a patient's mouth. Syringes typically have a hand piece for gripping by a hand of a dentist or dental assistant and a fitting adapted for receiving a detachable tube or tip. Such syringes are described in U.S. Pat. No. 5,927,975 and U.S. application Ser. No. 09/400,217, filed Sep. 21, 1999, which are hereby incorporated by reference. Fluids are conveyed through the hand piece and the fitting to the tip which delivers the fluids to the patient's mouth. The tip must be securely held by the fitting to prevent it from being ejected into the patient's mouth, and it must be clean to avoid spreading disease. To ensure the tips are clean, dentists typically change tips after each patient.

Ideally, a dentist should be able to quickly and securely lock a new tip in place. Unfortunately, many conventional syringes do not provide this ability. For instance, some fittings require that the tip have a circumferential groove extending around the exterior surface of the tip. These fittings hold the tip in place with ball bearings which engage the circumferential groove. To use these fittings, the dentist must first depress a collar to permit the ball bearings to move radially outwardly so the tip can be inserted, and thereafter allow the collar to return to a locking position wherein the ball bearings are moved inwardly to engage the groove and lock the tip in position. These steps require the dentist to use both hands and can be awkward. Further, if the collar has not properly returned to its locking position, the tip remains loose and may be ejected from the syringe, posing a potential safety hazard. Other fittings hold a tip in place with elastomeric O-rings which engage the circumferential groove. Although these fittings grip the groove automatically when a tip is inserted, they rely on elasticity of the O-rings and friction between the O-rings and the tip to oppose removal of the tip. Because the magnitude of the frictional force is relatively limited, the tip is subject to ejection from the fitting when exposed to a strong force. Further, O-rings degrade over time which can diminish their elasticity and ability to generate frictional force, making the fitting unreliable.

Another type of fitting is adapted for holding a tip which does not have a circumferential groove but rather has an exterior surface that is generally uniform in size and shape along the tip. These fittings frequently include a threaded retainer nut or locking cap which must be screwed on to lock the tip in place. The dentist must unscrew the retainer nut, hold the nut or set it aside while removing a used tip and inserting a clean tip, and then re-attach the retainer nut. These steps are awkward and time-consuming. Other fittings of this type have a collet or the like for gripping the exterior surface of the tip. These fittings can be adequate for some applications. However, when exposed to large forces, such as forces generated when large quantities of high pressure fluid pass through the tip, the grip of the collet may be overpowered and the tip ejected.

SUMMARY OF THE INVENTION

Among the several objects and features of the present invention may be noted the provision of a dental syringe fitting which automatically locks a syringe tip in place upon insertion into the fitting; the provision of such a fitting which precludes accidental ejection of the tip from the fitting; the provision of such a fitting which sealingly connects passageways in a hand piece to passageways in a tip; and the provision of such a fitting which is easy to use.

Briefly, apparatus of the present invention includes, in combination, a syringe tip and a fitting for releasably connecting the tip to a hand piece for delivering a fluid forward to a mouth of a patient. The hand piece has a passageway for delivering the fluid to a discharge end of the hand piece. The syringe tip comprises an elongate tube having an exterior surface and an interior passage extending through the tube for transporting the fluid to the patient. The exterior surface of the tip includes a portion having a generally constant size and uniform shape. The fitting comprises a body adapted to attach to the hand piece adjacent the discharge end. The body has a central opening sized and shaped for receiving the portion of the tip. Further, the fitting comprises a gripping mechanism mounted in the opening and having a plurality of locking fingers disposed around the opening. Each of the plurality of fingers includes a tooth extending inwardly into the opening. The tooth has a rearward facing point adapted to releasably engage the portion of the exterior surface of the tip when the tip is received in the opening and to prevent ejection of the tip from the opening due to forces applied to the tip by the fluid being transported through the tube to the patient. Thus, the tip is secured to the hand piece when the teeth engage the portion of the tip.

In another aspect, the present invention includes, in combination, a syringe tip and a fitting for releasably connecting the tip to a hand piece for delivering a fluid forward to a mouth of a patient. The hand piece has a passageway for delivering the fluid to a discharge end of the hand piece. The syringe tip comprises an elongate tube having an exterior surface and an interior passage extending through the tube for transporting the fluid to the patient. The exterior surface of the tip includes a portion having a generally constant size and uniform shape. The fitting comprises a body adapted to attach to the hand piece adjacent the discharge end. The body has a central opening sized and shaped for receiving the portion of the tip. The fitting further comprises a gripping mechanism mounted in the opening having a plurality of locking fingers resiliently biased inwardly around the opening. Each of the plurality of fingers includes a tooth extending inwardly into the opening to releasably engage the portion of the exterior surface of the tip when the tip is received in the opening and to prevent ejection of the tip from the opening due to forces applied to the tip by the fluid being transported through the tube to the patient. Thus, the tip is secured to the hand piece when the teeth engage the portion of the tip.

Other objects and features of the present invention will be in part apparent and in part pointed out hereinafter.

BRIEF DESCRIPTION OF THE DRAWINGS

Corresponding reference characters indicate corresponding parts throughout the views of the drawings.

DETAILED DESCRIPTION OF THE PREFERRED EMBODIMENT

Figure 1:
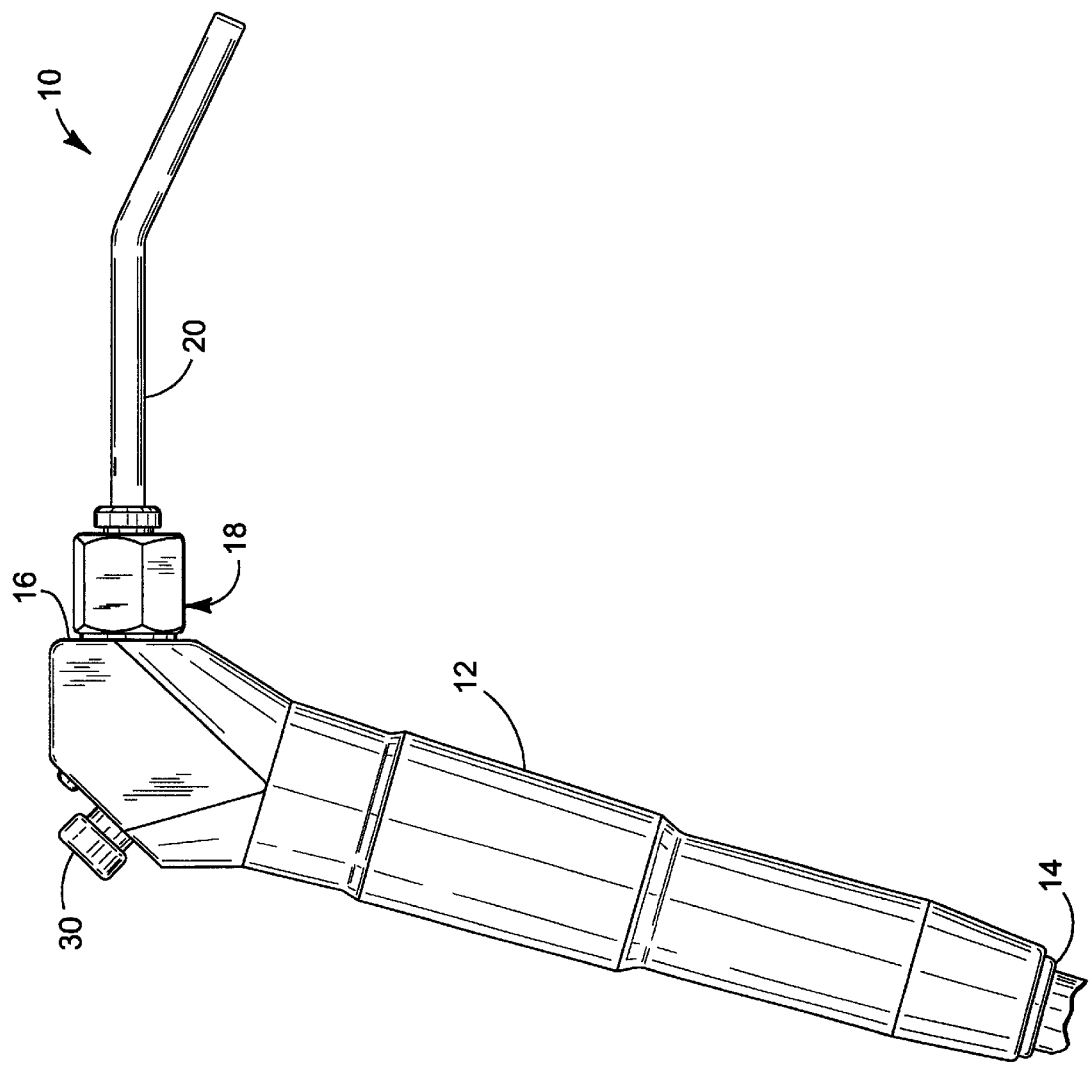
FIG. 1 is a side elevation of a dental syringe having a fitting and tip of the present invention.

Referring now to the drawings and in particular to FIG. 1, a dental syringe for delivering fluids to a mouth of a patient is indicated generally by the reference number 10. The syringe 10 includes a conventional hand piece 12 shaped for gripping and having an intake end 14 and a discharge end 16. A fitting, generally designated by 18, is attached to and extends from the hand piece 12 adjacent the discharge end 16. The fitting 18 is adapted for releasably connecting a tubular syringe tip 20 to the hand piece 12. The syringe tip 20 has a generally cylindrical exterior surface 22 and one or more interior passages for transporting fluids to the patient. The exterior surface 22 has at least one portion 24 which is generally constant in size and uniform in shape along the tip 20. For example, the portion may be cylindrical and have a constant diameter D. The exterior surface 22 is ideally made of a suitable malleable material such as a plastic, vinyl, or soft metal which permits positive engagement of locking teeth as described below.

Figure 2:
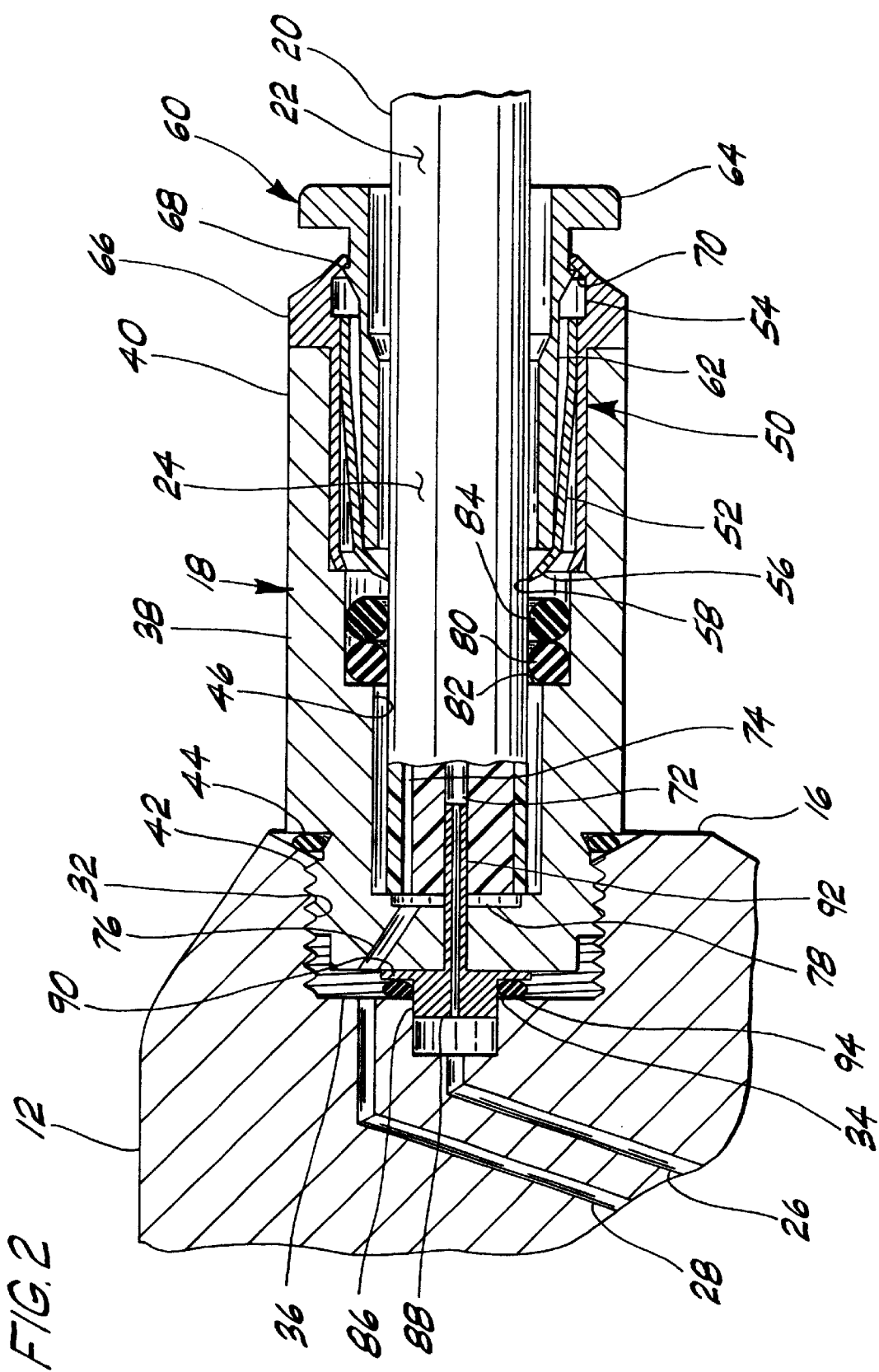
FIG. 2 is a partial vertical cross section of the syringe showing a first embodiment of the fitting and a gripping mechanism in a locking position.

As illustrated in FIG. 2, the hand piece 12 includes two separate internal passageways 26, 28 for conveying two fluids, such as compressed air and water, from the intake end 14 to the discharge end 16. Two valves (not shown) control fluid flow through the passageways. Button controls 30 (only one control is visible in FIG. 1) are provided on the hand piece 12 for operating the valves. The hand piece 12 has an internally threaded socket 32 at the discharge end 16 where both of the internal passageways 26, 28 terminate. The first passageway 26, typically for water, terminates in a central region 34 of the socket. The second passageway 28, typically for pressurized air, terminates generally toward an outer margin 36 of the socket. Because the hand piece 12 is conventional, it will not be described in further detail.

As shown in FIG. 2, the fitting 18 has a generally cylindrical body 38 having a forward end 40 and an externally threaded rearward end 42 for attaching the fitting to the socket 32 of the hand piece 12. In the preferred embodiment, the body 38 is of one piece construction. An elastomeric O-ring 44 circumferentially positioned around the body 38 near the threaded rearward end 42 prevents leakage between the hand piece and the body. Although the body 38 of the fitting 18 of the preferred embodiment is cylindrical, it may have other shapes such as hexagonal without departing from the present invention.

The body 38 has a central opening 46 sized and shaped for receiving the syringe tip 20, more specifically for receiving the portion 24 of the tip having constant size and uniform shape. The opening 46 is generally cylindrical and has a diameter which is larger than the diameter D of the tip portion 24. Although the opening 46 may have other diameters without departing from the scope of the present invention, the opening of the preferred embodiment has a diameter of about 0.157 inch for receiving tips 20 with portions 24 having a diameter of about 0.153 inch.

Figure 3:
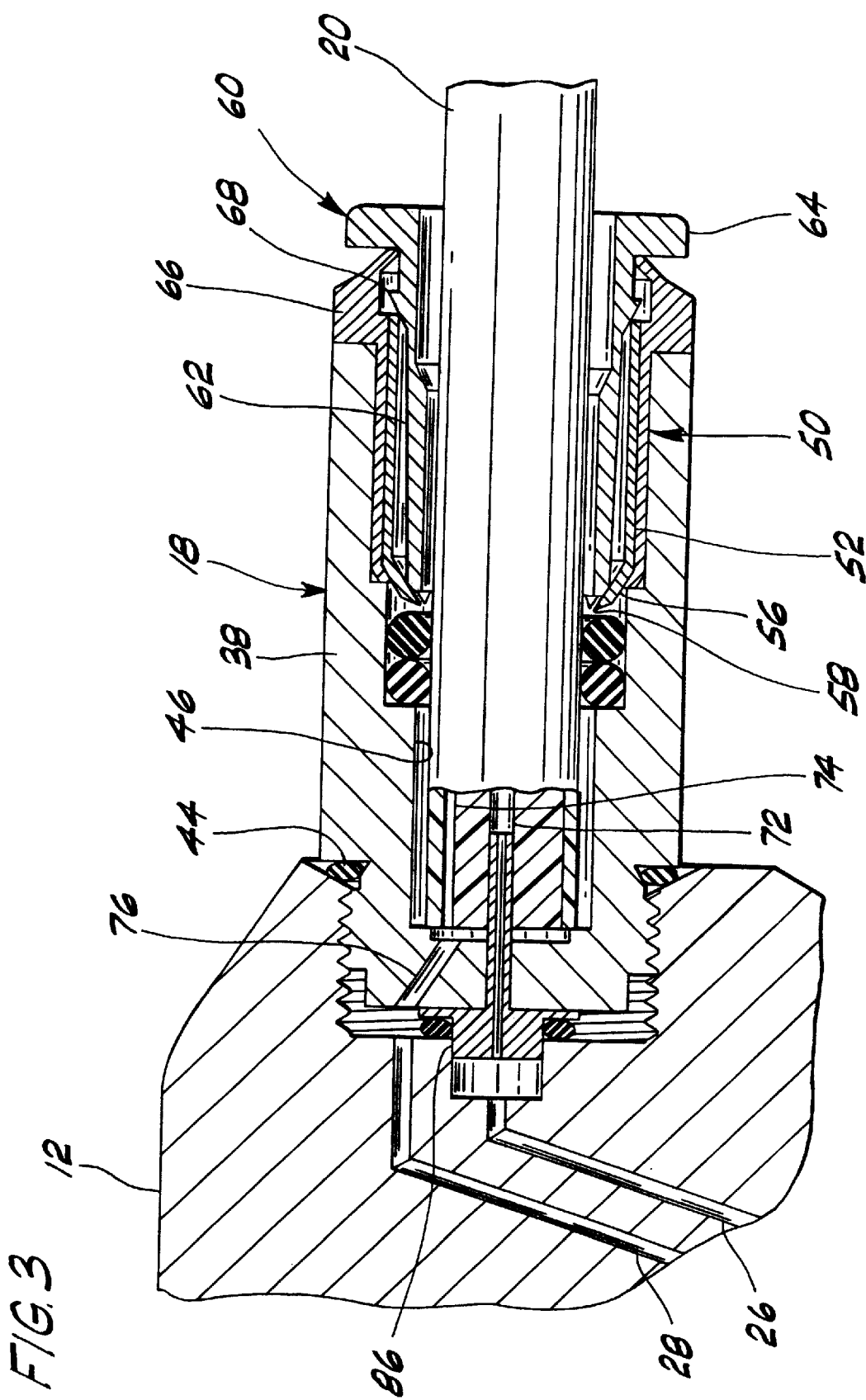
FIG. 3 is a partial vertical cross section showing the gripping mechanism in a releasing position.

A gripping mechanism, generally designated by 50, is mounted in the central opening 46 for gripping the syringe tip 20 and securing the tip to the fitting 18 and the hand piece 12. The gripping mechanism 50 includes a plurality of locking fingers 52 disposed around the opening and adapted to releasably engage the portion 24 when the tip is received in the opening. The locking fingers 52 are moveable between a locking position as shown in FIG. 2 in which the fingers engage the portion 24 to secure the tip 20 to the fitting 18 and a releasing position as shown in FIG. 3 in which the fingers disengage the portion to allow the tip to be removed from the fitting. The fingers 52 are resiliently biased radially inwardly toward the locking position. The gripping mechanism 50 is positioned in the body 38 at a location where its operation will not interfere with fluid connections between the two interior passageways 26, 28 and the tip 20.

Each of the locking fingers 52 extends rearwardly from a common retaining ring 54 located adjacent the forward end 40 of the body 38 to an inclined portion forming a tooth 56 extending radially inwardly into the opening 46. Each tooth 56 has a rearward facing point 58 at a rearward end of the finger 52 for engaging the tip 20. The points 58 of the locking fingers are positioned in the central opening 46 at an axial position which corresponds with an axial position of the portion 24 when the tip 20 is received in the opening. Further, the teeth 56 are resiliently biased inwardly to a diameter less than the diameter D of the tip portion 24 to ensure positive engagement. Although the teeth 56 of the preferred embodiment are positioned at rearward ends of the locking fingers 52, it is envisioned that the teeth could be located at other positions along the locking fingers without departing from the scope of this invention.

A release, generally designated 60, is provided for moving the teeth 56 between the locking position and the releasing position. The release 60 comprises a collar 62 which is coaxially aligned with the opening 46 and positioned inside the locking fingers 52. The collar 62 has a flange 64 which protrudes from the forward end 40 of the body 38 for manually pushing the collar toward the hand piece 12. When the flange 64 is pushed rearward, the collar 62 moves toward the rearward end 42 of the body 38 to the releasing position shown in FIG. 3 in which a rearward end of the collar engages a sloped surface on each tooth 56 to push the teeth outwardly and disengage them from the surface 22 of the tip.

The fingers 52 are resiliently biased inwardly, so that in the releasing position shown in FIG. 3, surfaces of the teeth press against the collar 62 to bias the collar toward the locking position. Thus, when not being pushed rearwardly, the collar 62 will automatically move to the locking position. The retaining ring 54 is attached to a housing 66 which surrounds the fingers 52 and collar 62. The housing 66 is press fit into the opening 46 to hold the gripping mechanism 50 in position. A circumferential ridge 68 on the collar 62 is captured in a groove 70 in the housing to prevent removal of the collar from the fitting 18.

The syringe tip 20 includes a first interior passage 72 for delivering the first fluid and a second interior passage 74 for delivering the second fluid. It is envisioned that the first or second interior passages 72, 74, respectively, could be formed of two or more generally aligned tubes within the tip 20, or formed of one tube within the tip as shown in the drawings. Although the tip 20 of the preferred embodiment has two passages, it is envisioned that the tip could have a single passage or more than two passages without departing from the scope of the present invention.

A passageway 76 extends through the rearward end 42 of the body 38 for delivering the second fluid from the discharge end 16 of the hand piece 12 at the outer margin 36 of the socket 32 to the central opening 46. In particular, the passageway 76 delivers the fluid through the body 38 to a recess 78 located at the rearward end 42 of the central opening. Fluid passes from the recess 78 into the second interior passage 74 of the tip 20.

An elastomeric O-ring 80 is mounted in the opening 46 against a shoulder 82 as shown in FIG. 2. The O-ring 80 encircles the opening for providing a fluid-tight sealing connection between the body 38 of the fitting and the exterior surface 22 of the tip. Further, a second O-ring 84 is included in series with the first O-ring 80 to improve the seal, although it is understood that there may be one or any number of O-rings without departing from the scope of the present invention.

A tubular connector 86 is provided at the rearward end 42 of the body for sealingly engaging the first interior passage 72 of the tip 20 when the tip is received in the opening to deliver fluid from the discharge end of the hand piece 12 to the first interior passage of the tip. The connector 86 comprises a base 88, a flange 90 extending from the base, and a tubular member 92 having a generally constant diameter sized for insertion into the first interior passage 72 of the tip 20 and for providing a fluid-tight sealing connection between the connector and the tip. The connector 86 is positioned between the fitting 18 and the hand piece 12, so the base 88 extends into the central region 34 of the socket and the tubular member 92 extends into the first interior passage 72 of the syringe tip. An opening extends through a central longitudinal axis of the connector 86 for providing fluid communication between the hand piece 12 and the first interior passage 72. The connector 86 is releasably and removably attached to the body 38 so the connector may be readily replaced. The connector 86 may have other configurations including that shown in the alternate embodiment of FIG. 4 where the base 88 does not extend into the central region 34 of the socket 32.

An elastomeric O-ring 94 is mounted against the flange 90 of the connector 86 and disposed around the passage for holding the connector in the fitting 18 and for providing a fluid-tight sealing connection between the connector and the hand piece 12.

In operation, the fitting 18 automatically locks the syringe tip 20 in the opening 46 when the tip is inserted and prevents accidental ejection of the tip from the fitting. When the tip 20 is pushed into the opening, the locking fingers 52 of the gripping mechanism 50, which are biased toward the locking position, automatically engage the exterior surface 22 of the tip. As the tip 20 is pushed farther into the opening, the tip passes through the O-rings 80, 84 and the first interior passage 72 slides over the tubular connector 86. When inserted, the teeth 56 engage the exterior surface 22 and secure the tip in the fitting.

The tip 20 is positively locked in place against forces tending to remove it from the fitting 18, especially forces caused by fluid pressure and fluid flow which tend to eject the tip. Any movement of the tip 20 in a forward direction away from the hand piece 12 as to remove the tip from the opening 46 causes the teeth 56, which positively engage the exterior surface 22, to bite into the tip. Due to the shape of the teeth 56 and particularly the rearward facing points 58, the teeth tend to grip the exterior surface 22 and prevent movement of the tip. A force applied on the tip 20 in a forward direction as to remove the tip from the opening 46 is opposed by a corresponding holding force due to the teeth 56 engaging the tip. Therefore the tip 20 is positively locked in the fitting 18. Further, the teeth 56 bite into the tip 20 in part because of their geometries or shapes and in part because of material properties of the tip. Thus, the fitting 18 is preferably used with tips 20 made from a variety of soft or malleable materials such as plastic, vinyl, or soft metal that permit the teeth to bite into the tip.

Upon insertion of the tip 20 into the opening 46, the internal passages 72, 74 within the tip are automatically and sealingly connected in fluid communication with the corresponding passageways 26, 28 in the hand piece. The syringe 10 is then ready for use in delivering one or both fluids from the hand piece 12 through the tip 20 to the mouth of the patient. When the dentist presses the first button control 30 to open the first valve, the first fluid is delivered from the intake end 14 of the hand piece to the discharge end 16 at the central region 34 of the socket 32, thereafter through the tubular connector 86 and into the first interior passage 72 of the tip and through the tip to the patient. When the dentist presses the second button control 30 to open the second valve, the second fluid is delivered from the intake end 14 of the hand piece to the discharge end 16 at the outer margin 36 of the socket. The second fluid then passes through the passageway 76 in the body to the recess 78, into the second interior passage 74 of the tip and thereafter through the tip to the patient.

After use the tip 20 is no longer clean and must be replaced. To remove the tip, the dentist applies force to the flange 64 of the release collar 62 to move the collar rearward and push the teeth 56 of the locking fingers 52 outward to disengage the teeth from the exterior surface 22 of the tip. The tip 20 is pulled out of the opening while applying the force to the flange 64.

The fitting permits connection to tips having a circumferential groove extending around the exterior surface of the tip (e.g., such as disclosed in U.S. application Ser. No. 09/400,217), instead of tips having a portion with a uniform shape. With a tip of this type, the locking fingers of the gripping mechanism engage the groove to hold the tip in place. The tip may be made of a rigid material, such as a hard metal, and the fingers hold the groove rather than biting into the tip.

Figure 4:
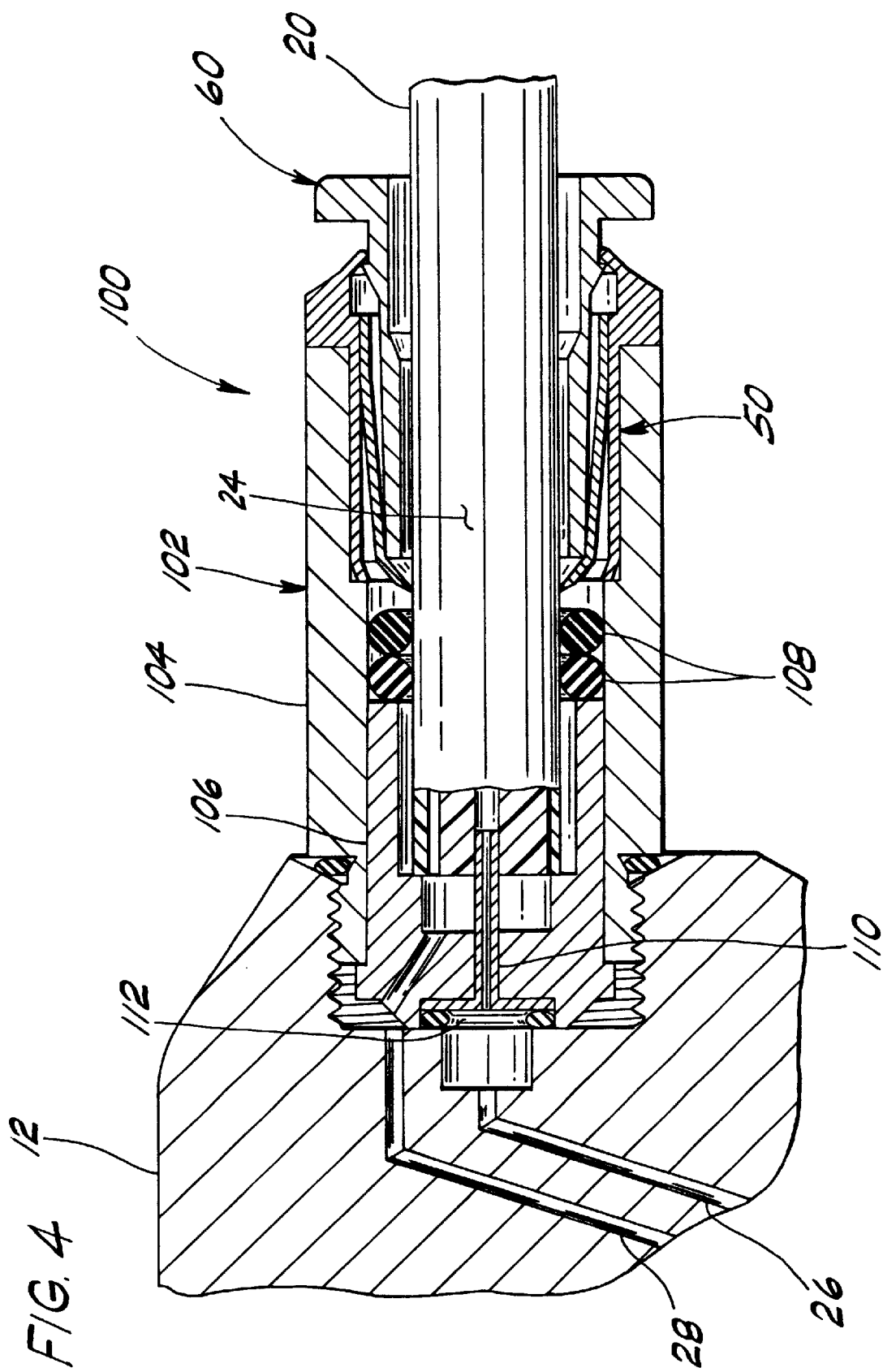
FIG. 4 is a partial vertical cross section showing a second embodiment of the fitting.

A second embodiment 100 of the fitting includes a body 102 constructed of two pieces, as shown in FIG. 4. The body 102 includes a generally cylindrical sleeve 104 and a cup-shaped insert 106. Two elastomeric O-rings 108 are mounted in the sleeve 104 forward of the insert 106. The O-rings 108 encircle the opening for providing a fluid-tight sealing connection between the sleeve 104 and the exterior surface 22 of the tip 20. A tubular connector 110 fits into a recess 112 in a rearward end of the insert 106. In other respects, the invention according to the second embodiment 100 shown in FIG. 4 is identical in structure and operation to the first embodiment shown in FIGS. 2 and 3.

Thus, the invention provides a dental syringe fitting 18 which automatically locks the syringe tip 20 in place upon insertion into the fitting, precludes accidental ejection of the tip, and simultaneously sealingly connects with two passageways 26, 28 in a hand piece 12 for the delivery of two fluids.

In view of the above, it will be seen that the several objects of the invention are achieved and other advantageous results obtained.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. In combination, a syringe tip and a fitting for releasably connecting the tip to a hand piece for delivering a fluid forward to a mouth of a patient, the hand piece having a passageway for delivering the fluid to a discharge end of the hand piece, the syringe tip comprising an elongate tube having an exterior surface and an interior passage extending through the tube for transporting the fluid to the patient, the exterior surface of the tip including a portion having a generally constant size and uniform shape, said portion having a substantially uniform diameter, and the fitting comprising a body adapted to attach to the hand piece adjacent the discharge end, the body having a central opening sized and shaped for receiving said portion of the tip, and a gripping mechanism mounted in the opening having a plurality of locking fingers disposed around the opening, each of said plurality of fingers including a tooth extending inwardly into the opening and having a rearward facing point adapted to releasably engage said portion of the exterior surface of the tip when the tip is received in the opening, said points being resiliently biased inwardly to a diameter less than said uniform diameter of said tip portion thereby automatically engaging the tip upon insertion of the tip into the opening and preventing ejection of the tip from the opening due to forces applied to the tip by the fluid being transported through the tube to the patient, thereby automatically securing the tip to the hand piece when the tip is inserted into the opening of the fitting.

2. A combination as set forth in claim 1 wherein the gripping mechanism further comprises a release which is moveable between a locking position in which the teeth engage said portion of the exterior surface to secure the tip to the fitting, and a releasing position in which the teeth disengage said portion of the exterior surface allowing the tip to be removed from the fitting.

3. A combination as set forth in claim 2 wherein the release comprises a collar having a flange for manually moving the collar between the locking position and the releasing position.

4. A combination as set forth in claim 3 wherein the collar pushes the locking fingers outward to disengage the exterior surface when the collar is in the releasing position.

5. A combination as set forth in claim 3 wherein the collar is biased toward the locking position.

6. A combination as set forth in claim 5 wherein each of said fingers includes a surface adapted to engage a rearward end of the collar when the collar is in the releasing position to bias the collar toward the locking position.

7. A combination as set forth in claim 1 further comprising a tubular connector adapted to sealingly engage the interior passage of the tip when the tip is received in the opening to deliver fluid from the discharge end of the hand piece to the interior passage of the tip.

8. A combination as set forth in claim 7 wherein the interior passage comprises a first interior passage for delivering a first fluid from the discharge end of the hand piece to the patient, and the tip further comprises a second interior passage for delivering a second fluid from the discharge end of the hand piece to the patient.

9. A combination as set forth in claim 8 wherein the fitting further comprises a passageway extending through the body for delivering the second fluid from the discharge end of the hand piece to the second interior passage of the tip.

10. A combination as set forth in claim 1 wherein said portion of the exterior surface of the tip is formed of a plastic material.

11. A combination as set forth in claim 1 wherein the body has an external threaded end for attaching the fitting to an internally threaded socket in the discharge end of the hand piece.

12. A combination as set forth in claim 1 wherein the body comprises at least two pieces.

13. A combination as set forth in claim 1 further comprising said hand piece.

14. In combination, a syringe tip and a fitting for releasably connecting the tip to a hand piece for delivering a fluid forward to a mouth of a patient, the hand piece having a passageway for delivering the fluid to a discharge end of the hand piece, the syringe tip comprising an elongate tube having an exterior surface and an interior passage extending through the tube for transporting the fluid to the patient, the exterior surface of the tip including a portion having a generally constant size and uniform shape, and the fitting comprising a body adapted to attach to the hand piece adjacent the discharge end, the body having a central opening sized and shaped for receiving said portion of the tip, and a gripping mechanism mounted in the opening having a plurality of locking fingers resiliently biased inwardly around the opening, each of said plurality of fingers including a tooth extending inwardly into the opening to releasably engage said portion of the exterior surface of the tip when the tip is received in the opening and to prevent ejection of the tip from the opening due to forces applied to the tip by the fluid being transported through the tube to the patient, each of said fingers automatically engaging the tip upon insertion of the tip into the opening thereby automatically securing the tip to the hand piece when the tip is inserted into the open in of the fitting.

15. A combination as set forth in claim 14 further comprising a release which is moveable between a locking position in which the teeth engage said portion of the exterior surface of the tip and a releasing position in which the teeth disengage the exterior surface.

16. A combination as set forth in claim 15 further comprising a tubular connector located within the central opening, the connector sized and shaped for being received in the interior passage of the tip when the tip is received in the opening.

* * * * *